United States Patent [19]

Cherkofsky et al.

[11] 4,198,421
[45] Apr. 15, 1980

[54] ANTIINFLAMMATORY 2-SUBSTITUTED-DIBENZO[2,3:6,7]OXEPINO[4,5-d]IMIDAZOLES

[75] Inventors: Saul C. Cherkofsky, Wilmington, Del.; Thomas R. Sharpe, Fort Salonga, N.Y.

[73] Assignee: E. I. Du Pont de Nemours and Company, Wilmington, Del.

[21] Appl. No.: 965,075

[22] Filed: Nov. 30, 1978

[51] Int. Cl.$^2$ .................. A61K 31/415; C07D 491/04
[52] U.S. Cl. ................................ 424/273 R; 260/333; 548/303; 548/323
[58] Field of Search ...................... 548/323; 424/273 R

[56] References Cited
U.S. PATENT DOCUMENTS 3,711,489   1/1973   Lombardino ........................ 548/323

FOREIGN PATENT DOCUMENTS 845074 2/1977 Belgium .

OTHER PUBLICATIONS

Lombardino J. Het. Chem. 1974, vol. 11, pp. 17–21.
Lombardino et al. J. Med. Chem. 1974, vol. 17, pp. 1182–1188.
Kametani et al. Chem. Abst. 1964, vol. 61, cols. 13278–132789.

Primary Examiner—Natalie Trousof

[57] ABSTRACT

Antiinflammatory 2-substituted-dibenzo[2,3:6,7]oxepino[4,5-d]imidazoles, such as 10-fluoro-2-[(1,1,2,2-tetrafluoroethyl)sulfonyl]-1H-dibenzo[2,3:6,7]oxepino[4,5-d]imidazole, useful for treating arthritis and related diseases.

18 Claims, No Drawings

ANTIINFLAMMATORY 2-SUBSTITUTED-DIBENZO[2,3:6,7]OXEPINO[4,5-d]IMIDAZOLES

BACKGROUND OF THE INVENTION

This invention relates to antiinflammatory 2-substituted-dibenzo[2,3:6,7]oxepino[4,5-d]imidazoles.

Belgian Pat. No. 845,074 discloses antiinflammatory 4,5-diaryl-2-(substituted-thio)imidazoles and their corresponding sulfoxides and sulfones.

Lombardino, in U.S. Pat. No. 3,707,475 discloses antiinflammatory 4,5-diaryl-2-substituted imidazoles.

Doebel, in U.S. Pat. Nos. 3,505,350 and 3,651,080, respectively, discloses antiinflammatory 4-alkyl-5-aryl-1-substituted-2-mercaptoimidazoles and 4-alkyl-2-alkylthio-5-aryl-1-substituted-imidazoles.

Zauer, K., et al., in *Chem. Ber.*, 106, 1638 (1973) disclose 4,5-bis(4-methoxyphenyl)-2-methylthioimidazole and 4,5-bis(4-chlorophenyl)-2-methylthioimidazole but do not suggest any use.

A number of references, such as *Current Sci. India*, 17, 184–85 (1948) and *Acta. Chem. Acad. Sci. Hung.*, 79 (2) 197–212 (1973) disclose 2-(substituted-thio)-4,5-diphenylimidazoles with substituents such as methyl, propyl, allyl, and acetonyl.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than presently available drugs.

SUMMARY OF THE INVENTION

This invention relates to novel antiinflammatory compounds, pharmaceutical compositions containing them, and methods of using them to treat arthritis in mammals. These compounds are of the formula:

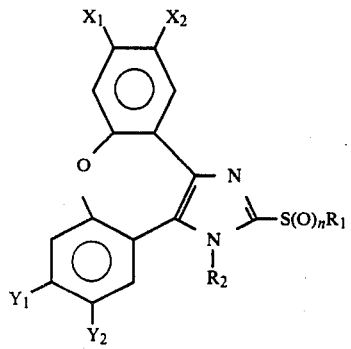

where
$n = 0, 1$ or $2$;
$R_1 = $ polyfluoro $C_1$–$C_2$ alkyl, provided at least two fluorine atoms are alpha to the sulfur atom;
$R_2 = H$,

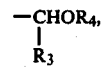

2-tetrahydropyranyl, 2-tetrahydrofuranyl,

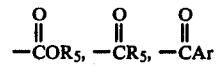

or $-SO_2Ar$;
$R_3 = H$ or methyl;
$R_4 = C_1$–$C_3$ alkyl, benzyl, $-CH_2CH_2OCH_3$ or

$R_5 = C_1$–$C_4$ alkyl or benzyl;
$Ar =$

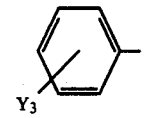

where $Y_3$ is H, F, Cl, Br, $C_1$–$C_4$ alkyl, $C_1$–$C_4$ alkoxy or nitro;
$X_1$ and $Y_1$ independently $= H$, F, Cl, dimethylamino or $C_1$–$C_2$ alkoxy;
$X_2$ and $Y_2$ independently $= H$, F or Cl; provided at least one of $X_1$, $X_2$, $Y_1$, $Y_2$ is other than H;
its pharmaceutically suitable acid addition salt where $n = 0$, or
its pharmaceutically suitable metal salt where $n = 1$ or 2.

Preferred Scope

Compounds of preferred scope are where, independently:
(a) $n = 2$; or
(b) $R_1 = CF_3$ or $CF_2CF_2H$; or
(c) $X_1$ and $Y_1$ independently $= H$, F, Cl or methoxy and
$X_2$ and $Y_2 = H$.

More preferred are compounds of the preceding scope where n, $R_1$, $X_1$, $Y_1$, $X_2$ and $Y_2$ are as defined. An example of a preferred compound is where:
$n = 2$,
$R_1 = CF_2CF_2H$,
$R_2 = H$,
$X_1 = F$,
$X_2 = H$,
$Y_1 = H$, and
$Y_2 = H$.

Pharmaceutical Salts

Pharmaceutically suitable salts of compounds where $n = 0$ include pharmaceutically suitable acid addition salts, preferably formed from mineral acids, and include hydrochloride, nitrate and sulfate. The acid preferably has a $pk_a$ value not greater than 2.5.

Pharmaceutically suitable salts of compounds where n=1 or 2 include those of certain metals, such as sodium, potassium, and calcium.

The salts can be prepared by well known methods in the prior art of preparing salts.

Synthesis

Preparation of compounds of formula IX below is described in conjunction with the following schematic. The substituent definitions, n, $R_1$, $R_2$, $X_1$, $X_2$, $Y_1$ and $Y_2$, are as previously defined.

Scheme I

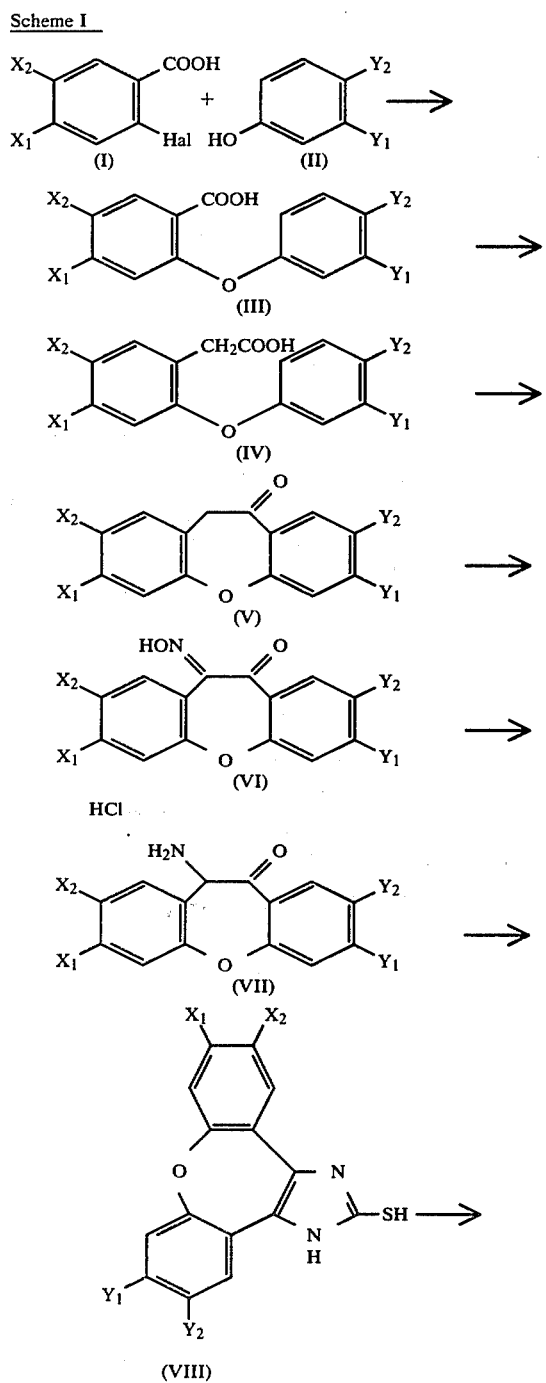

Scheme I -continued

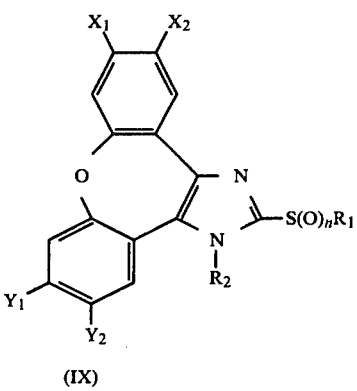

Compounds of structure (IX) can be prepared as follows: 10,11-dihydrodibenzo[b,f]oxepin-11-ones of structure (V) can be prepared starting with the appropriately substituted o-halobenzoic acids (I) and phenols (II) as described by M. Protiva et al. in Collect. Czech. Commun., 34 (8), 2258–2277 (1969).

The isonitrosoketones (VI) can be prepared by passing freshly generated methyl nitrite into a solution of the ketones (V) in ether in the presence of catalytic amounts of HCl. This procedure is analogous to the preparation of isonitrosopropiophenone from propiophenone as described by W. H. Hartung and F. Crossley, Org. Syntheses, Vol. II, p. 363.

The aminoketones (VII) are prepared by catalytic reduction in the presence of platinum dioxide. One suitable solvent for this reaction is tetrahydrofuran, to which is added gaseous HCl in order to convert the aminoketones in situ to the stable HCl salts. A similar reduction procedure is described by S. Kimoto et al. in Yakugaku Zasshi, 88 (10), 1323–1328 (1968).

Mercaptoimidazoles (VIII) can be prepared by reacting the aminoketones (VII) with potassium thiocyanate in acetic acid at temperatures in the range of 50°–118° C. This procedure for the synthesis of imidazoles is described in The Chemistry of Heterocyclic Compounds, Part I, Chapter III by K. Hofmann.

Scheme II

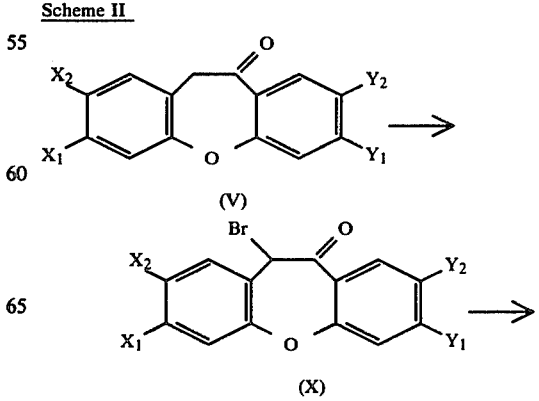

Scheme II
-continued

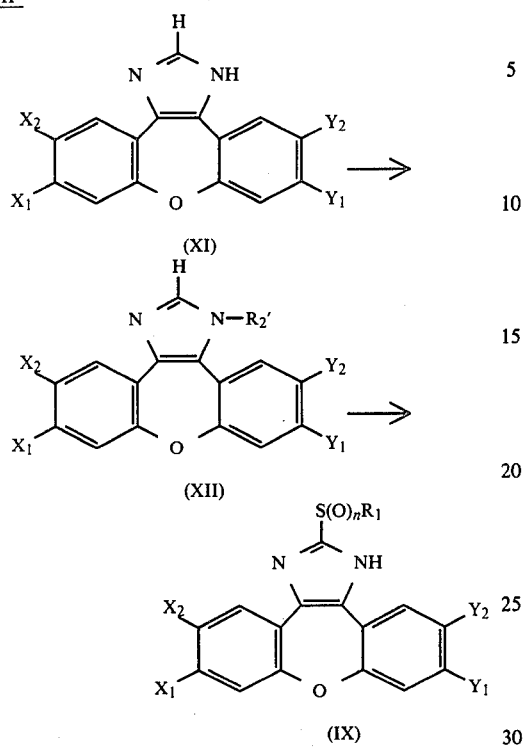

Alternately, the compounds of formula IX can be prepared as depicted in Scheme II by first converting the ketone V to the unsubstituted imidazole XI by conventional methods known in the art, such as bromination (to X) followed by reaction with formamide [H. Bredereck et al., Ber, 86 88(1953) and Ber, 92, 338(1959)]. Compound XI can then be reacted with an appropriate reagent such as benzyl chloromethyl ether, ethyl vinyl ether, 2-chlorotetrahydrofuran, dihydropyran, or benzenesulfonyl chloride to give a protected imidazole XII ($R_2' = -CH(R_3)OR_4$, 2-tetrahydropyranyl, 2-tetrahydrofurenyl, or $-SO_2Ar$). The resulting 1-(substituted)imidazole (XII) can then be treated with a strong base, such as n-butyl lithium, followed by a fluorinated alkylsulfenyl halide, disulfide, or sulfonic anhydride. Typical of these reagents are $CF_3SCl$, $CF_3SSCF_3$, and $(CF_3SO_2)_2O$. Optionally, the choice of the protecting group and the workup conditions allows isolation of the desired 2-(substituted thio or sulfonyl-)imidazole with $R_2=H$ directly. Compounds where $R_1=CF_3$ can be conveniently prepared by this method.

The 2-(substituted-thio)imidazole compound can be oxidized to the corresponding sulfoxide or sulfone by using oxidizing agents such as m-chloroperbenzoic acid [Tweit, R. C., et al., J. Med. Chem., 16, 1161 (1973)]. Other suitable oxidizing agents include sodium metaperiodate [Leonard, N. J. and Johnson, C. R., J. Org. Chem. 27, 282 (1962)], hydrogen peroxide [Kochergin, P. M. and Shchukina, M. N., J. Gen. Chem. U.S.S.R., 25, 2289 (1955)] and potassium permanganate [Rapp, K. E. et al., J. Am. Chem. Soc., 72, 3642 (1950)].

The appropriate $R_2$ substituent on the imidazole ring of the compounds of the invention can often by introduced by direct alkylation, acylation or sulfonylation of the compounds of formula IX where $R_2=H$. This reaction can be carried out in the absence or presence of a base, such as potassium carbonate, pyridine, triethylamine, potassium t-butoxide, methyl lithium or the like.

The reaction can be run neat, using the reagent as solvent, or in the presence of an inert solvent, including but not limited to dimethylformamide, glyme, tetrahydrofuran, pyridine and methylene chloride. The temperature of the reaction can be in the range from about $-78°$ C. to the boiling point of the solvent or reagent. Examples of alkylating, acylating and sulfonylating agents that can be employed are the following: alkoxymethyl halides, such as benzylchloromethyl ether; acyloxymethyl halides, such as chloromethylpivalate; dihydropyran; ethyl vinyl ether; 2-chlorotetrahydrofuran; alkyl chloroformates, such as ethyl chloroformate; alkanoic anhydrides and alkanoyl halides- such as acetic anhydride; aroyl halides, such as benzoyl chloride; arylsulfonyl halides, such as benzenesulfonyl chloride.

In the following examples, all parts are by weight and degrees are in centrigrade unless otherwise stated.

EXAMPLE 1

10-Fluoro-2-[(1,1,2,2-tetrafluoroethyl)thio]-1H-dibenzo[2,3:6,7]-oxepino[4,5-d]imidazole

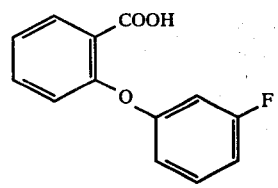

(a) 2-(3-Fluorophenoxy)benzoic acid o-Iodobenzoic acid (12.4 g.) and nitrobenzene (5 ml.) were treated under stirring at 140°-150° with 3.4 g. of anhydrous potassium carbonate; the mixture was stirred for 10 minutes at 160°, and 3-fluorophenol (7 g.) was added, followed by portionwise addition of potassium carbonate (7 g.) and copper powder (0.1 g.) The mixture was stirred at 160°-165° for 45 minutes, cooled, diluted with water, and treated with 5 N HCl to give the title compound, m.p. 122°.

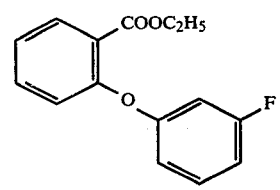

(b) Ethyl 2-(3-Fluorophenoxy)benzoate 2-(3-Fluorophenoxy)benzoic acid (10 g.) and 100 ml of ethanol containing 1 ml. of concentrated $H_2SO_4$ were heated at reflux through molecular sieves overnight. The solvent was evaporated, and the residue poured into 50 ml. of 7% $NaHCO_3$. The resulting ester was extracted with ether.

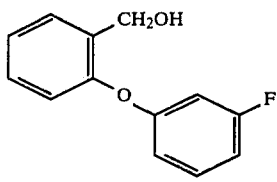

(c) 2-(3-Fluorophenoxy)benzenemethanol

Ethyl 2-(3-fluorophenoxy)benzoate (37 g.) dissolved in 90 ml. of ether, was added dropwise to a suspension of lithium aluminum hydride (4.5 g.) in 350 ml of ether. The reaction mixture was heated to reflux for 6 hours to give, after work-up, 30 g. of the title compound.

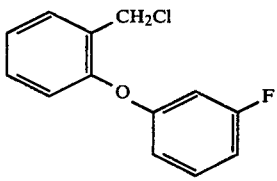

(d) 1-(Chloromethyl)-2-(3-fluorophenoxy)benzene 2-(3-Fluorophenoxy)benzenemethanol (30 g.) was mixed with 13.2 ml. of pyridine. Thionyl chloride (12.4 ml.) was added dropwise at 25°–30°, the mixture stirred 5 hours at room temperature, then partitioned between water and ether. The organic layer was washed with a 10% sodium carbonate solution, then with water, dried over sodium carbonate and evaporated to give the title compound.

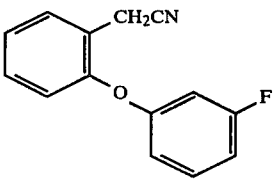

(e) 2-(3-Fluorophenoxy)benzeneacetonitrile 1-(Chloromethyl)-2-(3-fluorophenoxy)benzene (26.5 g.) was dissolved in 300 ml of ethanol; a solution of sodium cyanide (7.8 g.) in 15 ml of water was added, and the resulting mixture was heated to reflux overnight. The ethanol was evaporated, the residue taken up in water, extracted with ether and the combined ether extracts were dried and concentrated to give the title compound.

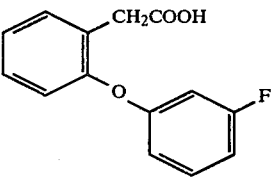

(f) 2-(3-Fluorophenoxy)benzeneacetic Acid 2-(3-Fluorophenoxy)benzeneacetonitrile (23 g.), dissolved in 80 ml of ethanol, was heated to reflux for 2 hours with a solution of 20 g. potassium hydroxide in 40 ml of water. The ethanol was evaporated, the residue taken up in water, extracted with ether and acidified to give the title compound, m.p. 81°–84°.

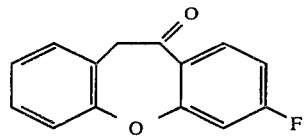

(g) 7-Fluorodibenz[b,f]oxepin-10(11H)-one 2-(3-Fluorophenoxy)benzeneacetic acid (22 g.) was added to 90 g. of polyphosphoric acid at 125°. The reaction mixture was stirred 1 hour at 125°. It was then cooled; water (300 ml) was added with stirring; a solid product was filtered and extracted with toluene several times. The combined toluene extracts were washed successively with water, dilute alkali, and water, then dried over magnesium sulfate and evaporated to yield the title compound as a solid product, which was purified upon treatment with hexane.

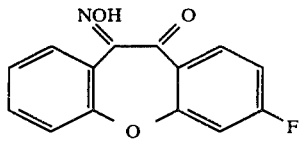

(h) 3-Fluorodibenz[b,f]oxepin-10,11-dione-10-monooxime

Methyl nitrite, generated upon addition of a solution of conc. sulfuric acid (3 ml.) and water, (6 ml.) to a mixture of sodium nitrite (5.8 g.), methanol (3.6 ml.), and water (3.4 ml.), was bubbled through a solution of 7-fluorodibenz[b,f]oxepin-10(11H)-one (16 g.) in 200 ml. of ether and 1 ml. of conc. HCl at such a rate that the ether came to gentle refluxing. When the addition of methyl nitrite was completed, the reaction mixture was stirred at room temperature for 2 hours, then extracted with alkali. The alkaline solution was acidified with dilute HCl to give the title compound, m.p. 196°–198°.

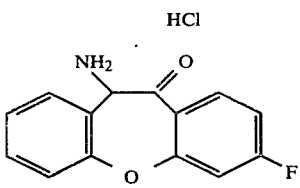

(i) 11-Amino-7-fluorodibenz[b,f]oxepin-10(11H)-one Hydrochloride

3-Fluorodibenz[b,f]oxepin-10,11-dione-10-monooxime (10 g.), dissolved in 120 ml of THF containing 100 mg. of platinum dioxide, was shaken in a Parr hydrogenator for 6 hours; the resulting hydrochloride salt was dissolved upon addition of 400 ml of methanol, the catalyst was filtered off and the solution was evaporated in vacuo. The solid residue was triturated with acetone to give the title compound in crystalline form.

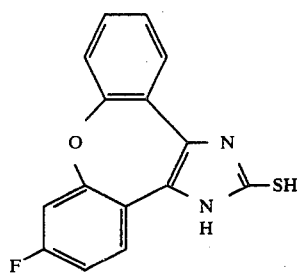

(j)
10-Fluoro-1H-dibenzo[2,3:6,7]oxepino[4,5:d]-imidazole-2-thiol

11-Amino-7-fluorodibenz[b,f]oxepin-10(11H)-one hydrochloride (8 g) was suspended in acetic acid (120 ml); potassium thiocyanate (2.82 g) was added and the reaction mixture was heated to reflux. After 10 minutes complete solution was obtained and shortly thereafter a solid began to separate. Heating was continued for 15 minutes. After cooling, the solid product was collected by filtration, washed with water and dried to give 10-fluoro-1H-dibenzo[2,3:6,7]oxepino[4,5-d]-imidazole-2-thiol; m.p. 299°–300°.

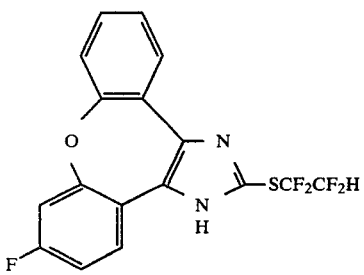

(k)
10-Fluoro-2-[(1,1,2,2-tetrafluoroethyl)thio]-1H-dibenzo[2,3:6,7]oxepino[4,5-d]imidazole To a mixture of 5.4 g. of the above thiol, 1.9 g of diisopropylamine and 110 ml. DMF in a pressure vessel was added 3.8 g. of tetrafluoroethylene. The mixture was shaken and heated at 50° for 8 hours, then cooled and vented. The reaction mixture was poured onto ice water; the solid product was collected, washed with water, dried and recrystallized from hexane to give 10-fluoro-2-[(1,1,2,2-tetrafluoroethyl)thio]-1H-dibenzo[2,3:6,7]oxepino[4,5-d]imidazole, m.p. 172°–175°.

EXAMPLE 2

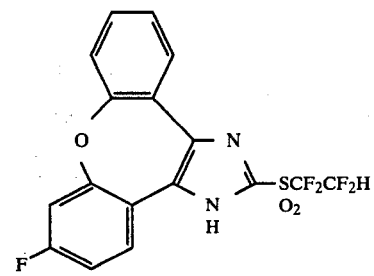

10-Fluoro-2-[(1,1,2,2-tetrafluoroethyl)sulfonyl]-1H-dibenzo[2,3:6,7]oxepino[4,5-d]imidazole To a solution of the product of Example 1-k (4.4 g) in 50 ml. methylene chloride was added portionwise m-chloroperoxybenzoic acid (5.6 g). The mixture was stirred at room temperature overnight, it was then diluted with 30 ml. THF, and washed a few times with 10% sodium bicarbonate solution. The organic layer was dried and concentrated on a rotary evaporator. The residue was recrystallized from toluene to give the title compound, m.p. 171°–173°.

Following the procedures of Examples 1 and 2 with substitution of the appropriate starting materials, the compounds in the following table can be prepared.

| $X_1$ | $X_2$ | $Y_1$ | $Y_2$ | $R_1$ | $R_2$ | n | m.p. |
|---|---|---|---|---|---|---|---|
| F | H | H | H | $CF_2CHF_2$ | H | 0 | 172°–175° |
| F | H | H | H | $CF_2CHF_2$ | H | 1 | |
| F | H | H | H | $CF_2CHF_2$ | H | 2 | 171°–173° |
| F | H | H | H | $CF_2CHF_2$ | $COOC_2H_5$ | 0 | |
| F | H | H | H | $CF_3$ | H | 2 | |
| $(CH_3)_2N$ | H | $OCH_3$ | H | $CF_2CH_2F$ | H | 2 | |
| H | H | $OC_2H_5$ | H | $CF_2CHF_2$ | H | 2 | |
| Cl | H | H | H | $CF_2CHF_2$ | H | 2 | |
| Cl | H | Cl | H | $CF_2CHF_2$ | H | 2 | |
| H | Cl | H | Cl | $CF_3$ | 2-tetrahydropyranyl | 0 | |

-continued

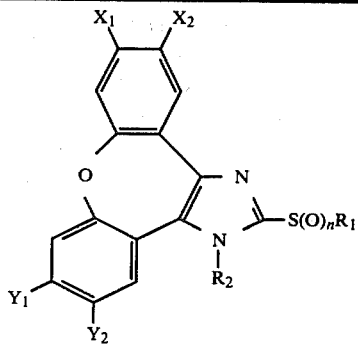

| $X_1$ | $X_2$ | $Y_1$ | $Y_2$ | $R_1$ | $R_2$ | n | m.p. |
|---|---|---|---|---|---|---|---|
| F | H | F | H | $CF_2CHF_2$ | 2-tetra-hydro-furanyl | 0 | |
| $OCH_3$ | H | H | H | $CF_3$ | $COC_6H_5$ | 0 | |
| $OC_2H_5$ | H | Cl | H | $CF_3$ | $CH_2OCH_2CH_2OCH_3$ | 0 | |
| F | H | $OCH_3$ | H | $CF_2CHF_2$ | $SO_2C_6H_5$ | 0 | |
| F | H | H | H | $CF_2CHF_2$ | $C(O)$—⟨C₆H₄⟩—Cl | 0 | |
| F | H | Cl | H | $CF_3$ | $C(O)$—⟨C₆H₄⟩—Br | 0 | |
| Cl | Cl | H | H | $CF_2CHF_2$ | $SO_2$—⟨C₆H₄⟩—$CH_3$ | 0 | |
| F | H | $OCH_3$ | H | $CF_3$ | $C(O)$—⟨C₆H₄⟩—$NO_2$ | 0 | |
| F | Cl | H | H | $CF_3$ | $C(O)$—⟨C₆H₄⟩—$OCH_3$ | 0 | |
| Cl | Cl | Cl | H | $CF_2CHF_2$ | $COCH_3$ | 0 | |

Dosage Forms

The anti-arthritic agents of this invention which have anti-inflammatory properties can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to about 100 milligrams per kilograms of body weight. Ordinarily 0.5 to 50 and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a Standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 275 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

To detect and compare the antiinflammatory activities of compounds in this series and standard drugs, a test was used based on a standard model of arthritis for which there is good correlation with human efficacy. The model is adjuvant-induced arthritis in rats. Federation Proceedings, Vol. 32, No. 2 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Nonarthritic controls are injected with mineral oil. The animals are held for two weeks to allow development of arthritis. Paw volumes (uninjected, left hind paw) are measured and the adjuvant injected rats are culled and distributed to treatment groups of 10 of equal disease severity. Nonarthritic controls are distributed to two groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the six following days. One day after the last dose the paw volumes (uninjected, left hind paw) are measured using a Ugo Basile Volume Differential Meter Model 7101.

$$\frac{\left(\begin{array}{c}\text{Arthritic Control}\\\text{Mean Paw Volume (ml)}\end{array}\right) - \left(\begin{array}{c}\text{Treatment Group}\\\text{Mean Paw Volume (ml)}\end{array}\right)}{\left(\begin{array}{c}\text{Arthritic Control}\\\text{Mean Paw Volume (ml)}\end{array}\right) - \left(\begin{array}{c}\text{Non-Arthritic Control}\\\text{Mean Paw Volume (ml)}\end{array}\right)} \times$$

100 = % Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table II.

Compounds from this series were also compared to indomethacin, phenylbutazone, ibuprofen, and aspirin.

TABLE II

| Established Adjuvant-Induced Arthritis in Rats (A.A.) | |
|---|---|
| Chemical Example Number | A. A. ED50% mg/kg |
| 1 (k) | <27 |
| 2 | 4.5 |
| Indomethacin | 0.3 |
| Phenylbutazone | 10 |
| Ibuprofen | 100 |
| Aspirin | 305 |

"Consisting essentially of" in the present disclosure is intended to have its customary meaning: namely, that all specified material and conditions are very important in practicing the invention but that unspecified materi-

What is claimed is:
1. A compound of the formula

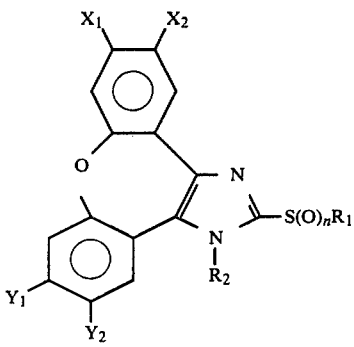

where
n = 0, 1 or 2;
$R_1$ = polyfluoro $C_1$-$C_2$ alkyl, provided at least two fluorine atoms are alpha to the sulfur atom;
$R_2$ = H,

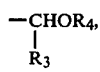

2-tetrahydropyranyl, 2-tetrahydrofuranyl,

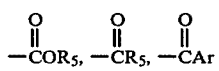

or —$SO_2Ar$;
$R_3$ = H or methyl;
$R_4$ = $C_1$-$C_3$ alkyl, benzyl, —$CH_2CH_2OCH_3$ or

$R_5$ = $C_1$-$C_4$ alkyl or benzyl;
Ar =

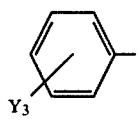

where $Y_3$ is H, F, Cl, Br, $C_1$-$C_4$ alkyl, $C_1$-$C_4$ alkoxy or nitro;
$X_1$ and $Y_1$ independently = H, F, Cl, dimethylamino or $C_1$-$C_2$ alkoxy;
$X_2$ and $Y_2$ independently = H, F or Cl; provided at least one of $X_1$, $X_2$, $Y_1$, $Y_2$ is other than H;
its pharmaceutically suitable acid addition salt where n = 0 or its pharmaceutically suitable metal salt where n = 1 or 2.

2. A compound of claim 1 where n = 2.
3. A compound of claim 1 where
$R_1$ = $CF_3$ or $CF_2CF_2H$.
4. A compound of claim 1 where
$X_1$ and $Y_1$ independently = H, F, Cl or methoxy; and
$X_2$ and $Y_2$ = H.
5. A compound of claim 1 where
n = 2;
$R_1$ = $CF_3$ or $CF_2CF_2H$;
$R_2$ = H;
$X_1$ and $Y_1$ independently = H, F, Cl or methoxy; and
$X_2$ and $Y_2$ = H.
6. The compound of claim 1 where
n = 2;
$R_1$ = $CF_2CF_2H$;
$R_2$ = H;
$X_1$ = F;
$X_2$ = H;
$Y_1$ = H; and
$Y_2$ = H.
7. A pharmaceutical composition consisting essentially of a suitable pharmaceutical carrier and an effective antiinflammatory amount of a compound of claim 1.
8. A pharmaceutical composition consisting essentially of a suitable pharmaceutical carrier and an effective antiinflammatory amount of a compound of claim 2.
9. A pharmaceutical composition consisting essentially of a suitable pharmaceutical carrier and an effective antiinflammatory amount of a compound of claim 3.
10. A pharmaceutical composition consisting essentially of a suitable pharmaceutical carrier and an effective antiinflammatory amount of a compound of claim 4.
11. A pharmaceutical composition consisting essentially of a suitable pharmaceutical carrier and an effective antiinflammatory amount of a compound of claim 5.
12. A pharmaceutical composition consisting essentially of a suitable pharmaceutical carrier and an effective antiinflammatory amount of a compound of claim 6.
13. A method of treating arthritis in a mammal which comprises administering to the mammal an effective antiarthritic amount of a compound of claim 1.
14. A method of treating arthritis in a mammal which comprises administering to the mammal an effective antiarthritic amount of a compound of claim 2.
15. A method of treating arthritis in a mammal which comprises administering to the mammal an effective antiarthritic amount of a compound of claim 3.
16. A method of treating arthritis in a mammal which comprises administering to the mammal an effective antiarthritic amount of a compound of claim 4.
17. A method of treating arthritis in a mammal which comprises administering to the mammal an effective antiarthritic amount of a compound of claim 5.
18. A method of treating arthritis in a mammal which comprises administering to the mammal an effective antiarthritic amount of a compound of claim 6.

* * * * *